United States Patent [19]
Reich et al.

[11] Patent Number: 5,931,165
[45] Date of Patent: *Aug. 3, 1999

[54] FILMS HAVING IMPROVED CHARACTERISTICS AND METHODS FOR THEIR PREPARATION AND USE

[75] Inventors: Cary J. Reich, Los Gatos; Donald G. Wallace, Menlo Park; Greg Dapper, Newark, all of Calif.

[73] Assignee: Fusion Medical Technologies, Inc., Mountain View, Calif.

[ * ] Notice: This patent is subject to a terminal disclaimer.

[21] Appl. No.: 08/795,744

[22] Filed: Feb. 6, 1997

Related U.S. Application Data

[63] Continuation-in-part of application No. 08/673,710, Jun. 19, 1996, abandoned, application No. 08/481,712, Jun. 7, 1995, Pat. No. 5,690,675, and application No. 08/303,336, Sep. 6, 1994, Pat. No. 5,749,895

[60] Provisional application No. 60/028,807, Oct. 16, 1996, abandoned.

[51] Int. Cl.⁶ .................................................. A61B 19/00
[52] U.S. Cl. ........................................... 128/898; 606/229
[58] Field of Search ................................... 606/229, 5, 6, 606/213–215; 128/898, DIG. 8; 602/904; 623/11

[56] References Cited

U.S. PATENT DOCUMENTS

| | | |
|---|---|---|
| 4,378,017 | 3/1983 | Kosugi et al. . |
| 4,453,939 | 6/1984 | Zimmerman et al. . |
| 4,603,695 | 8/1986 | Ikada et al. . |
| 4,674,488 | 6/1987 | Nashef et al. . |
| 4,854,320 | 8/1989 | Dew et al. ................................. 606/3 |
| 4,889,722 | 12/1989 | Sheffield et al. . |
| 4,911,926 | 3/1990 | Henry et al. . |
| 4,937,254 | 6/1990 | Sheffield et al. . |
| 4,937,270 | 6/1990 | Hamilton et al. . |
| 4,973,466 | 11/1990 | Reich . |
| 5,017,229 | 5/1991 | Burns et al. . |
| 5,053,388 | 10/1991 | Gibson et al. . |
| 5,068,225 | 11/1991 | Pennell et al. . |
| 5,071,417 | 12/1991 | Sinofsky . |
| 5,124,155 | 6/1992 | Reich . |
| 5,126,141 | 6/1992 | Henry . |
| 5,134,229 | 7/1992 | Saferstein et al. . |
| 5,135,751 | 8/1992 | Henry et al. . |

(List continued on next page.)

FOREIGN PATENT DOCUMENTS

| | | |
|---|---|---|
| 0 372 969 | 6/1990 | European Pat. Off. . |
| 0 416 250 | 3/1991 | European Pat. Off. . |
| 0 426 368 | 5/1991 | European Pat. Off. . |
| 0 608 139 | 7/1994 | European Pat. Off. . |
| 0 608 921 | 8/1994 | European Pat. Off. . |
| 0 610 731 | 8/1994 | European Pat. Off. . |
| 0 645 150 | 3/1995 | European Pat. Off. . |
| 0 669 138 | 8/1995 | European Pat. Off. . |
| WO 92/20349 | 11/1992 | WIPO . |
| WO 92/21354 | 12/1992 | WIPO . |
| WO 92/22312 | 12/1992 | WIPO . |
| WO 93/13137 | 7/1993 | WIPO . |
| WO 93/16687 | 9/1993 | WIPO . |
| WO 93/17669 | 9/1993 | WIPO . |
| WO 94/02517 | 2/1994 | WIPO . |
| WO 94/08635 | 4/1994 | WIPO . |
| WO 95/09883 | 4/1994 | WIPO . |
| WO 94/21324 | 9/1994 | WIPO . |
| WO 94/24962 | 11/1994 | WIPO . |
| WO 95/15343 | 5/1995 | WIPO . |
| WO 95/15747 | 6/1995 | WIPO . |

*Primary Examiner*—Mickey Yu
*Assistant Examiner*—Kelly O'Hara
*Attorney, Agent, or Firm*—Townsend and Townsend and Crew LLP

[57] ABSTRACT

Gelatin film compositions are useful for immobilization over tissue, usually by the application of energy to the films. Exemplary films comprise cross-linked and non-cross-linked granular and non-granular gelatin sheets, typically including a plasticizer. The gelatin films are dry, thin, and preferably meet certain pliability, elasticity, melting temperature, and other criteria. Methods are described for producing these films from collagen. Methods are further described for applying these films to tissue.

16 Claims, 9 Drawing Sheets

U.S. PATENT DOCUMENTS

| | | |
|---|---|---|
| 5,156,613 | 10/1992 | Sawyer . |
| 5,156,839 | 10/1992 | Pennell et al. . |
| 5,171,318 | 12/1992 | Gibson et al. . |
| 5,194,473 | 3/1993 | Shinoda et al. . |
| 5,201,745 | 4/1993 | Tayot et al. . |
| 5,209,776 | 5/1993 | Bass et al. . |
| 5,259,998 | 11/1993 | Reich . |
| 5,264,540 | 11/1993 | Cooper et al. . |
| 5,266,326 | 11/1993 | Barry et al. . |
| 5,274,028 | 12/1993 | Bertrand et al. . |
| 5,281,660 | 1/1994 | Bryhan et al. . |
| 5,321,113 | 6/1994 | Cooper et al. . |
| 5,356,883 | 10/1994 | Kuo et al. . |
| 5,364,622 | 11/1994 | Franz et al. . |
| 5,366,735 | 11/1994 | Henry . |
| 5,380,536 | 1/1995 | Hubbell et al. . |
| 5,410,016 | 4/1995 | Hubbell et al. . |
| 5,422,376 | 6/1995 | Webb . |
| 5,503,638 | 4/1996 | Cooper et al. ............................ 623/11 |
| 5,690,675 | 11/1997 | Sawyer et al. ......................... 606/229 |

FILMS HAVING IMPROVED CHARACTERISTICS AND METHODS FOR THEIR PREPARATION AND USE

This application is a continuation-in-part of Provisional Application Ser. No. 60/028,807, filed on Oct. 16, 1996 now abandoned; and is a continuation-in-part of application Ser. Nos. 08/673,710, filed on Jun. 19, 1996 now abandoned; 08/481,712 filed on Jun. 7, 1995 now U.S. Pat. No. 5,690,675; and Ser No. 08/303,336, filed on Sep. 6, 1994 now U.S. Pat. No. 5,749,895. The full disclosures of each of these applications are incorporated herein by reference.

BACKGROUND OF THE INVENTION

1. Field of the Invention

The present invention relates generally to collagen and gelatin compositions and methods for their preparation and use. In particular, the present invention relates to a gelatin film having characteristics suitable for application to tissue for a variety of purposes.

The use of biological materials for the sealing of wounds and other defects in tissue as well as the inhibition of tissue adhesion has been proposed. For example, the use of collagen patches for closing wounds and creating an anastomoses has been suggested in U.S. Pat. Nos. 5,071,417; 5,156,613; 5,209,776. U.S. Pat. No. 5,156,613, is assigned to the Assignee of the present application, and describes the immobilization of collagen-containing patch material to tissue using radio frequency and laser energy.

Numerous procedures and materials have been proposed to minimize or eliminate post-surgical adhesions. Such procedures include introducing barrier materials such as metals, polymers, and natural materials over the target site. A woven material of regenerated cellulose is currently marketed for this purpose by Johnson & Johnson under the trademark Interceed®. A film of hyaluronic acid is also available under the trademark Seprafilm™ (Genzyme Corp, Cambridge, Mass.) This product, however, is not attached to tissue and remains unfixed in vivo. Other polymeric materials that have been tried for this purpose include nylon, cellophane, PTFE, polyethylene, siloxane, elastomers and polylactic acid copolymer films. Many of these materials are not biodegradable and therefore, remain in the body with unpredictable and potentially undesirable consequences.

Of particular interest to the present invention, gelatin or collagen films have been applied to tissue for tissue sealing. Specific gelatin materials are described in parent application Ser. Nos. 08/303,336 and 08/481,712, the full disclosures of which have previously been incorporated herein by reference.

To be effective for use over tissue in order to seal the tissue, prevent adhesion, or for any other purpose, collagen or gelatin films should possess a number of characteristics. They should be sufficiently thin so that they can be effectively bonded to the underlying tissue by the subsequent application of energy. They should be sufficiently pliable so that they can conform to the tissue, further enhancing bonding to the tissue upon subsequent application of energy. They should possess low moisture, enhancing their preservation and permitting rehydration upon application to tissue. They should be sufficiently elastic, still further enhancing conformability to tissue. They should be sufficiently strong so that they can be bonded to tissue and can provide the desired sealing after bonding. They should possess melting temperatures which facilitate fusion and bonding to tissue upon the application of energy. Different embodiments of the present invention will meet at least some of these objectives.

2. Description of the Background Art

WO 93/17669 describes particular hydrogel materials that may be applied to tissue, cross-linked by exposure to UV, and relied on for inhibiting tissue adhesion. U.S. Patents relating to materials and methods for inhibiting tissue adhesion include U.S. Pat. Nos. 5,422,376; 5,410,016; 5,380,536, 5,366,735; 5,364,622; 5,365,883; 5,321,113; 5,266,326; 5,264,540; 5,194,473; 5,156,839; 5,135,751; 5,134,299; 5,126,141; 5,068,225; 5,017,229; 4,937,270; 4,937,254; 4,911,926; 4,889,772; 4,674,488; and 4,603,695. Published PCT applications relating to materials and methods for inhibiting tissue adhesion include WO 95/15747; WO 95/15343; WO 95/09883; WO 94/24962; WO 94/21324; WO 94/08635; WO 94/02517; WO 93/16687; WO 93/13137; WO 92/22312; and WO 92/21354. Published European applications relating to materials and methods for inhibiting tissue adhesion include 669 138; 645 150; 610 731; 608 921; 608 139; 426 368; 416 250; and 372 969. Other patents relating to applying energy to fusible materials to wound treatment include U.S. Pat. No. 5,071,417; U.S. Pat. No. 5,156,613; and U.S. Pat. No. 5,209,776. Co-pending related applications assigned to the assignee of the present application include U.S. Ser. Nos. 08/303,336; 08/461,227; 08/461,228, 08/481,712; and 60/011,898, the full disclosures of which are incorporated herein by reference. Application Ser. Nos. 08/303,336 and 08/481,712, were published on Mar. 14, 1996, as WO 96/07355 and WO 96/07356, respectively.

SUMMARY OF THE INVENTION

The present invention provides improved film compositions composing gelatin and/or collagen are useful for a variety of purposes, including immobilization over tissue for tissue sealing and/or inhibition of tissue adhesion. The films are characterized by a film thickness in the range from 0.03 mm to 0.2 mm, preferably being from 0.055 mm to 0.075 mm, and a pliability in the range from 1.0 mN to 4.0 mN, preferably from 2 mN to 3.5 mN. In addition to these two characteristics, the gelatin films will be further characterized by at least one characteristic selected from the group consisting of (1) a moisture content in the range from 11% to 16%, preferably from 13% to 15%, (2) an elasticity in the range from 30% to 150%, preferably from 40% to 130%, (3) a tensile strength in the range from 150 N/cm$^2$ to 260 N/cm$^2$, preferably from 170 N/cm$^2$ to 250$^2$ N/cm, (4) a melting temperature in the range from 33° C. to 40° C., preferably from 34° C. to 37° C., (5) a collagenase digestion time in the range from 10 minutes to 40 minutes, preferably from 15 minutes to 35 minutes, and (6) a degree of swelling (V/V$_o$) in the range from 4.5 to 6.5, preferably from 5 to 6. Such films may be cross-linked or non-cross-linked, preferably being cross-linked. The gelatin films may further be granular or non-granular, preferably being granular. Still further, the films may comprise a plasticizer or be free from plasticizers. The films will preferably comprise mostly or entirely gelatin, with collagen being present at less than 10% by weight, more preferably less than 1% by weight. Preferred gelatin films according to the present invention will be cross-linked, granular, and include a plasticizer, as described in greater detail below.

In an alternative aspect, gelatin and/or collagen films according to the present invention comprise a sheet of granular, cross-linked gelatin and/or collagen (preferably gelatin) having a plasticizer content in the range from 5% by weight to 40% by weight, and a thickness in the range from 0.030 mm to 0.2 mm. Such films will usually consist essentially of gelatin and/or collagen, preferably gelatin, and the plasticizer, more preferably where the gelatin has been produced from collagen and residual collagen may be present to a low level, typically below 30% by weight, preferably below 1% by weight. Suitable plasticizers include polyethylene glycol, sorbitol, glycerine, and the like. The preferred plasticizer is polyethylene glycol with an average molecular weight of 400 (PEG 400), present in the film from 5% by weight to 40% by weight.

In yet another aspect, the present invention provides packages comprising gelatin or collagen films as described above present in a container. The container maintains the sterility and moisture of the film, so that the films are ready for surgical use immediately upon being removed from the containers. Virtually any type of sterile medical container would be suitable, with sterile pouches formed from moisture-impermeable materials, such as spun olefin, mylar, and the like, being exemplary.

In yet another aspect of the present invention, a method for sealing tissue comprises positioning the film as described above over a target region in tissue. Energy is then applied to the film while positioned over the region in an amount sufficient to immobilize the film on the tissue. The target region will typically be a surgical site, and the target tissue be any of a wide variety of tissue types such as muscle, skin, epithelial tissue, connective or supporting tissue, nerve tissue ophthalmic and other sense organ tissue, vascular and cardiac tissues, gastrointestinal organs and tissue, pleura and other pulmonary tissue, kidney, endocrine glands, male and female reproductive organs, adipose tissue, liver, pancreas, lymph, cartilage, bone, oral tissue, mucosal tissue and the like. The methods will be particularly useful for treating surgical sites in a target region, where the surgical site may be open or may have been sutured, stapled, or otherwise closed prior to permitting the tissue surface to engage an adjacent tissue surface. The method of the present invention for positioning the gelatin or collagen film over a surgical site is intended primarily for sealing the site or for inhibiting or preventing the occurrence of tissue adhesions between adjacent tissue surfaces. As used hereinafter and in the claims, the terms "inhibiting", and "inhibition" will denote both total inhibition (i.e. prevention) and partial inhibition of adhesion.

The methods of the present invention can rely on the application of energy from a wide variety of sources, including electromagnetic energy, particularly electric energy, e.g. radio frequency (RF) energy and microwave energy, infrared (heat) energy, and ultraviolet energy; optical energy, e.g. laser; mechanical energy, e.g. ultrasonic; and the like. Preferred is the use of RF energy which can be provided by conventional electrosurgical power supplies operating at frequencies typically in the range of 200 kHz to 1.2 MHz. Particularly preferred is the use of RF energy applicators which provide a uniform, dispersed energy flux over a defined area, such as inert gas beam RF energy sources, more particularly argon beam RF energy sources. Standard electrocautery devices could also find use.

The energy is applied in a pattern and manner suitable to immobilize the gelatin and/or collagen film over the target region so that the film remains in place while the tissue surface heals. In the case of preformed films, sheets, and the like, it is necessary only to selectively apply energy to local areas (e.g. spots, lines, etc.) on the matrix material surface in order to "tack" the material to the underlying tissue. That is, in the region where energy has been applied, the film will bond or otherwise fuse to the underlying tissue. In other regions, however, the film will not be bound directly to the tissue, but will remain immobilized as a result of those areas where the film or sheet of material is bound. For example, the energy may be applied about the periphery of the preformed film or sheet in order to attach the edges of the sheet to tissue. Additional locations within the periphery may also be tacked by applying spots or other small areas of energy to the material. It will also be possible to apply the energy uniformly to the film or sheet, thus resulting in substantially uniform bonding of the material to underlying tissue.

The methods of the present invention may be performed in conventional open surgical procedures, i.e. where access to internal body tissues and/or organs is provided through a relatively large percutaneous surgical incision which permits the introduction of conventional surgical instruments. The gelatin and/or collagen films of the present invention may thus be introduced by the surgeon while directly viewing the target region through the incision and manipulating the film using conventional graspers and the like. Alternatively, the methods of the present invention for sealing tissue may be performed via less invasive surgery, e.g. laparoscopically, thoracoscopically, arthroscopically, or the like. Such procedures typically rely on forming small percutaneous penetrations and accessing the target region through cannulas placed within such penetrations. The target region is viewed through an associated viewing scope. In both open surgical procedures and less invasive procedures, the films will typically be cut into a desired configuration and dimensions prior to application over the tissue.

In yet another aspect of the present invention, gelatin and/or collagen, preferably gelatin films are prepared by combining collagen and a plasticizer in an aqueous solution. Preferably, the collagen is at from 60% by weight to 95% by weight, preferably from 70% by weight to 90% by weight, and the plasticizer is present at from 5% by weight to 40% by weight, preferably from 8% by weight to 20% by weight. The solution is then heated to a temperature and for a time sufficient to convert the collagen to gelatin, preferably with at least about 90% by weight of the collagen being converted. Usually the solution will be heated to a temperature in the range from 65° C. to 75° C., preferably about 70° C. for a time in the range from 40 minutes to 60 minutes, preferably about 50 minutes. The converted solution is then formed into a thin layer and dried to produce a film. The film is then cross-linked, typically by exposure to radiation, such as ultraviolet radiation at a power from 100 mJ/cm$^2$ to 7000 mJ/cm$^2$, preferably from 2800 mJ/cm$^2$ to 4000 mJ/cm$^2$. The methods may further comprise packaging the films in sterile, moisture-type containers, where the moisture is maintained in the range from 10% to 17%, preferably from 11.5% to 16% by weight.

BRIEF DESCRIPTION OF THE DRAWINGS

FIG. 2A: Granular film. 1.2 mg film at 11% moisture plus saline to 13 mg total, enthalpy of denaturation, 15.7 J/g. FIG. 2B: Beef muscle; 11 mg hydrated. FIG. 2C: Porcine lung pleura; 9 mg hydrated. d. Porcine lung pleura and parenchyma; 8.5 mg hydrated. Films were hydrated m 0.9% aq. sodium chloride.

FIGS. 4A–4C. Non-granular film properties as a function of the degree of cross-linking.

FIGS. 5A–5C.

FIGS. 6A–6C. Bonding of apposed films pressed between heated brass blocks. All tests were on granular films, cross-linked with UV light for 20 min. Points marked with a vertical arrow represent films which failed cohesively at that force; i.e. the peel bond strength was higher than the measured point.

DETAILED DESCRIPTION OF THE SPECIFIC EMBODIMENTS

As used hereinafter and in the claims, the term "gelatin" refers to denatured collagen. Gelatin is a heterogenous mixture of high molecular weight water-soluble proteins, usually obtained by heating aqueous solutions of collagen or collagen-containing materials, such as skin, tendons, ligaments, etc. Gelatins may be commercially obtained from suppliers, such as Hormel foods, (Austin, Minn.). Preferably, the gelatin films of the present invention will be prepared by heating aqueous solutions of at least partially purified collagens, as described in detail in the Experimental section hereinafter. Collagen may be obtained from commercial suppliers, such as Kensey Nash (Type F, Exton, Pa.). A preferred collagen starting material is Type F collagen obtained from Kensey-Nash corporation.

As used hereinafter and in the claims, the terms "film" refers to sheet, layer, membrane, patch, or other generally planar configuration of the gelatin material. The films, or at least a substantial portion thereof, will have a thickness in the range from 0.01 mm to 0.20 mm, preferably from 0.04 mm to 0.08 mm. The thickness will usually be uniform, but not necessarily so. That is, the film thickness may vary within the aforestated ranges, and certain portions of the film may have thicknesses outside of these ranges, where the portions having such non-conforming thicknesses will generally not be intended for application to tissue. That is, they may be intended merely to facilitate handling of the films, or for other purposes. Film thickness may be measured by conventional means, such as a Mitutoyo Thickness Gauge Model, IDC Mitutoyo Corp., Japan or by weighing the film and calculating the thickness given the surface area of the film and the film density.

As used hereinafter and in the claims, the term "pliability" refers to the force required to bend the film through a defined distance. Pliability is measured in units of milliNewtons (mN), and specific methods for measuring pliability are set forth in the Experimental section hereinbelow.

As used hereinafter and in the claims, the phrase "moisture content" refers to the amount of water present in the gelatin films after preparation. The moisture content will be in the range from 10% by weight to 17% by weight, preferably being in the range from 11.5% by weight to 16% by weight. Moisture content can be measured in a variety of ways, such as weight loss on drying. The relatively dry collagen films of the present invention will typically hydrate when applied to tissue. The capability of the films hydrating may be assessed by the "degree of swelling" which is defined as $V/V_o$, where $V_o$ is volume when dry and V is volume when fully hydrated. The gelatin films of the present invention have a degree of swelling of at least 4.5, usually being in the range from 4.5 to 6.5, preferably in the range from 5 to 6.

As used hereinafter in the claims, the term "elasticity" refers to the percent strain at failure as described in detail in the Experimental section hereinafter.

As used hereinafter in the claims, the phrase "tensile strength" refers to the force required to induce tensile failure in the film. Tensile strength is measured in Newtons (N/cm$^2$) and particular methods for measuring tensile strength are set forth in the Experimental section hereinafter.

As used hereinafter in the claims, the phrase "melting temperature" refers to the denaturation temperature (DSC peak), i.e. the temperature at which the gelatin components of the gelatin and/or collagen films denature. Specific techniques for measuring such melting temperatures are set forth in the Experimental section hereinafter.

As used hereinafter in the claims, the phrase "collagenase digestion" refers to digestion of the protein films in a collagenase enzyme solution. Film samples having a particular size are placed in a collagenase solution having a particular activity. The time necessary for disintegration of the film samples is then determined. Specific techniques for measuring collagenase digestion times are set forth in the Experimental section hereinafter.

The gelatin and/or collagen films of the present invention may be cross-linked or non-cross-linked. The films are preferably cross-linked in a conventional manner, typically by exposure to radiation, such as ultraviolet (UV) radiation for a time and at a power level sufficient to achieve a desired level of cross-linking. Preferably, the films are cross-linked sufficiently to enhance tensile strength, handling characteristics, and resistance to degradation in the surgical environments in which they are used, without being cross-linked to the extent that the ability to fuse the films to underlying tissue is diminished.

The gelatin and/or collagen films of the present invention may also be granular or non-granular. By "granular" it is meant that the solution of denatured collagen has not been filtered or centrifuged prior to casting into films. Typically, the granular films will include collagen particles having a size greater than 0.01 mm, usually greater than 0.1 mm, prior to the heat conversion to gelatin. In contrast, non-granular gelatin films will be produced by filtration or by centrifugation of the collagen solutions to remove particles having sizes above 0.1 mm, usually above 0.03 mm, prior to film formation. Granular collagen films have been found to possess a significantly greater tear strength. Granular films are generally preferred for use as sealants because, for example, they shrink less with application of energy. Non-granular films are generally preferred to use as anti-adhesive barriers.

The gelatin and/or collagen, preferably gelatin, films of the present invention will preferably further include plasticizers, such as polyethylene glycol, sorbitol, glycerine, or the like. The plasticizers may be combined with the collagen solutions prior to heating and conversion to gelatin. The plasticizers enhance the pliability of the resulting gelatin films. The preferred plasticizer is polyethylene glycol having a molecular weight of about 400 which is present in the gelatin film at from 5% by weight to 40% by weight.

The films of the present invention may be applied to tissue using energy of a type and in an amount sufficient to fuse the gelatin material to underlying tissue. Suitable energy sources include electromagnetic energy, particularly electrical energy, e.g. radio frequency (RF) energy and microwave energy, infrared (heat) energy, and ultraviolet energy; optical energy, e.g. laser; mechanical energy, e.g. ultrasonic; and the like. Preferred are the use of RF energy sources, such as those available as electrosurgical power supplies from companies such as Valleylab, Boulder, Colo., and Birtcher Medical Systems, Irvine, Calif., employing conventional RF-applying probes. Particularly preferred are radio frequency energy sources which provide for a dispersed or distributed current flow from a hand-held probe to the tissue. One such radio frequency energy source referred to as an inert gas beam coagulator, relies on flow of an inert ionizable gas, such as argon, for conducting current from the probe to the tissue.

Energy from the energy source will typically be manually directed to the fusible material overlying the tissue using a probe connected to an external power supply. The treating physician will manually direct the probe to apply energy over the surface of the fusible material and will visually confirm that fusion has been achieved. The probe may use conventional electrosurgical power supplies having an energy output from 2 W to 100 W, preferably from 20 W to 60 W. The fusible material will typically be exposed to the energy for a total time from about 5 seconds to 120 seconds, usually from 10 seconds to 40 seconds, for material having an area from 1 cm$^2$ to 10 cm$^2$. The precise timing will depend on the physician's visual assessment that fusion of the material to the underlying tissue has been achieved.

Films according to the present invention may be prepared by first combining a collagen starting material, e.g. a commercial grade of collagen, with a plasticizer in a aqueous solution. Collagen starting materials may be obtained from any of the commercial sources listed above, and the preferred polyethylene glycol 400 plasticizer may be obtained from, for example, Polysciences, Inc., Warrington, Pa. The collagen is typically present at from 70% by weight to 90% by weight and the plasticizers present in from about 8% by weight to 20% by weight. Collagen and plasticizer are combined in a sterile water source, such as distilled water, deionized water, or the like. To prepare non-granular collagens, the collagen suspension may be filtered or centrifuged after heating as described in detail in the Experimental section hereinafter.

After the optional homogenization step, aqueous solution is heated to a temperature and for a time efficient to convert collagen largely or completely to gelatin. Typically, the solution is heated to a temperature in the range from 65° C. to 75° C., preferably about 70° C., for a time in the range from 40 minutes to 60 minutes. Any conventional heating vessel may be used for this reaction.

After heating and conversion of the collagen to gelatin, the solution is dried and formed into a film, preferably by pouring the solution into an appropriate receptacle, usually a square or rectangle. The solution may be dried at room temperature or an elevated temperature, preferably at room temperature at a moderate humidity, e.g. RH 50%. The films are then preferably cross-linked as described above.

Figure 7:
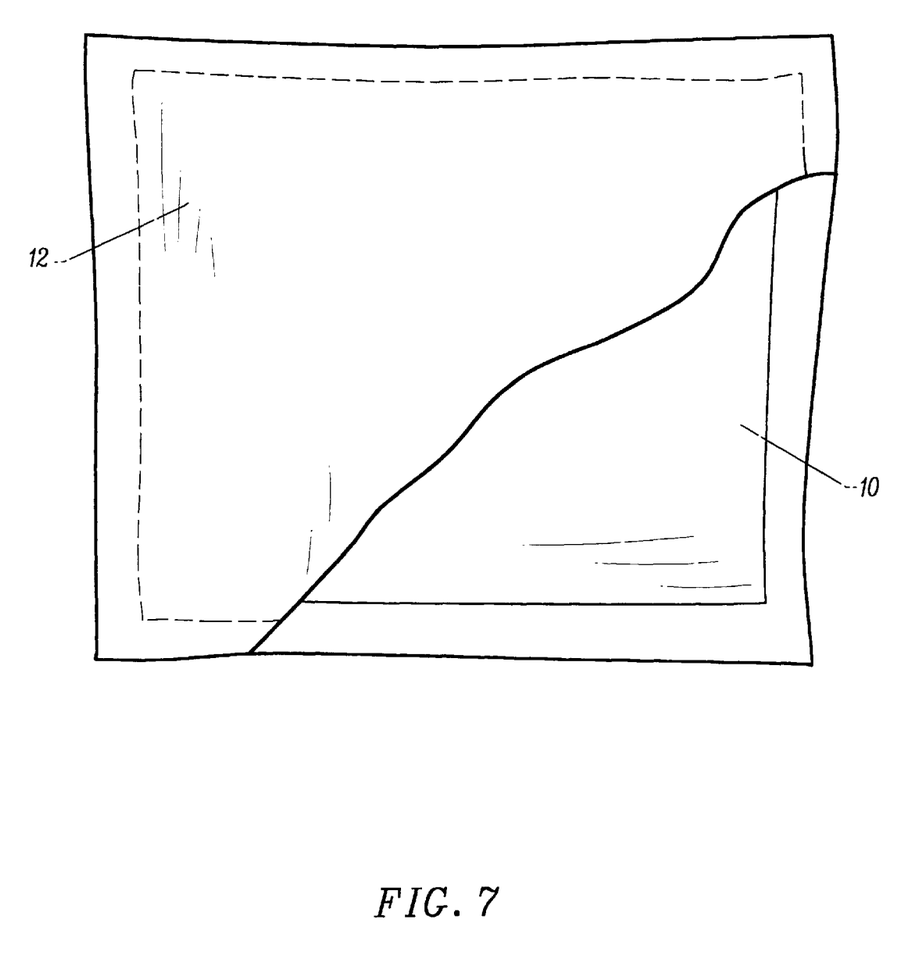
FIG. 7 illustrates a gelatin film according to the present invention packaged in a sterile surgical package.

Referring now to FIG. 7, a gelatin film 10 according to the present invention may be packaged in any conventional sterile packaging, such as a sterile pouch 12 comprising a moisture-impermeable material, such as mylar film. Such sterile packages are ready for use by the treating physician in the surgical environment.

The following examples are offered by way of illustration, not by way of limitation.

Experimental

EXAMPLE 1

Materials and Methods For Gelatin Film Production With UV Cross-Linking

Film materials were produced as follows:

Formulation A: 451 g grams of collagen (Kensey Nash Type F) Exton, Pa.) and 90 g of PEG 400 MW were added with 4500 mL WFI in a 5 liter reaction vessel. The solution was stirred and heated to 70° C. for 50 minutes. The material was then homogenized for 50 minutes at 20,000 RPM, using a Virtis Cyclone IQ$^2$ (Gardner, N.Y.) with a 20 mm flow-through head. The solution was filtered through a 100 µm polypropylene mesh. Water was added to adjust the percent solids to 3.8% (W/W). The solution was cooled to 35° C., and aliquots of 13 mL were cast into 100×15 mm sterile square polystyrene petri dishes. The gelled solution was dried at approximately 20° C. and 50% RH to form films with water content of 11–15% W/W. The films were cross-linked with 3500 mJ/cm$^2$ in a SPECTROLINKER XL1500 UV cross-linker equipped with 254 nm low pressure mercury bulbs.

Formulation B: 156.0 grams of collagen (Kensey Nash Type F) Exton, Pa.) was added to 18.1 lg of PEG 400 MW and 1500 ml WFI in a 2 liter reaction vessel. The solution was stirred and heated to 70° C. for 50 minutes. The material was then homogenized, filtered, and adjusted as in Formulation A above. The solution was then cooled to 35° C., and aliquots of 13 mL were cast into 100×15 mm sterile square polystyrene petri dishes. The solution was dried at approximately 20° C. and 50% RH to form films. The films were cross-linked with 3500 mJ/cm$^2$ in a SPECTROLINKER XL1500 UV cross-linker equipped with 254 nm low pressure mercury bulbs.

Formulation C: 36.1 g of collagen (Kensey Nash Type F) were dispersed with 960 ml WFI and 3.6 g PEG 400 MW and heated at 70° C. for 50 min. The dispersion was then homogenized as described in Formulation A and B. The homogenized dispersion without filtration or addition of water was cooled to 35° C. and cast into gels, dried, and cross-linked with 3000 mJ/cm$^2$ as described above.

Formulation D: 58.8 g of collagen as above were dispersed with 1850 ml WFI and 7.2 g PEG 400 MW and heated at 70° C. for 50 min. The formulation was then homogenized as in A & B above. The homogenized dispersion without filtration or the addition of water was then cooled to 35° C. and aliquots of 14.7 ml were cast into 100×1 mm sterile square polystyrene petri dishes. The gelled solution was dried as above, then cross-linked with 3300 mJ/cm$^2$ as above.

The formulations are summarized in Table 1 below.

TABLE 1

| Formulation | Collagen | Plasticizer % by weight | UV Xlinked in mJ/cm² |
|---|---|---|---|
| A | Kensey Nash collagen 65% | PEG 400 35% | 3500 |
| B | 89.6% | 10.4% | 3500 |
| C | 90% | 10% | 3000 |
| D | 89% | 11% | 3300 |

EXAMPLE 2

Characterization of Films Prepared in Example 1

Ten physical characteristics of the test film formulations were measured as follows.

1. THICKNESS

A Mitutoyo Thickness Gauge Model, IDC Mitutoyo Corp., Japan was used to determine the thickness of collagen/gelatin films. Using the release cable or the lifting lever, the thicknesses at each corner and at the center of the film were measured, for a total of 5 measurements on each film.

2. PERCENT SWELL

The amount of saline absorbed by collagen/gelatin during a 22±1 hour incubation was determined as follows. Saline solution (0.9% w/w; 5 mL) was added to each scintillation vial containing a test sample. The films were hydrated for 22±1 hours at 20–25° C. The degree of swelling was expressed as $V/V_o$, where V is the hydrated volume (weight) and $V_o$ is the dry volume (weight).

3. DENATURATION TEMPERATURE (DSC PEAK)

The denaturation temperature of the collagen/gelatin components of the test films and collagen raw material were determined using a DSC 2910 Differential Scanning Calorimeter (DSC), TA Instruments, New Castle, Del. 1.0–3.0 mg of film sample plus 0.9% w/w sodium chloride and hermetically sealed. Heating rates were 5° C./min. or 10° C./min. Peak temperatures and enthalpy of melting were recorded.

4. PLIABILITY

The pliability of each collagen/gelatin film was determined as follows. The force required to bend the collagen/gelatin film through a defined distance was measured, and the bending modulus calculated from the equation given in the Machinery's Industrial Press, Inc., NY, 21st Edition, 1980. A film sample was placed in the clamp on a Swiss Height Gauge so that 8 mm of patch was free. The force required to bend the patch through a deflection of 2 mm was measured.

5. TEAR TEST

Figure 1:
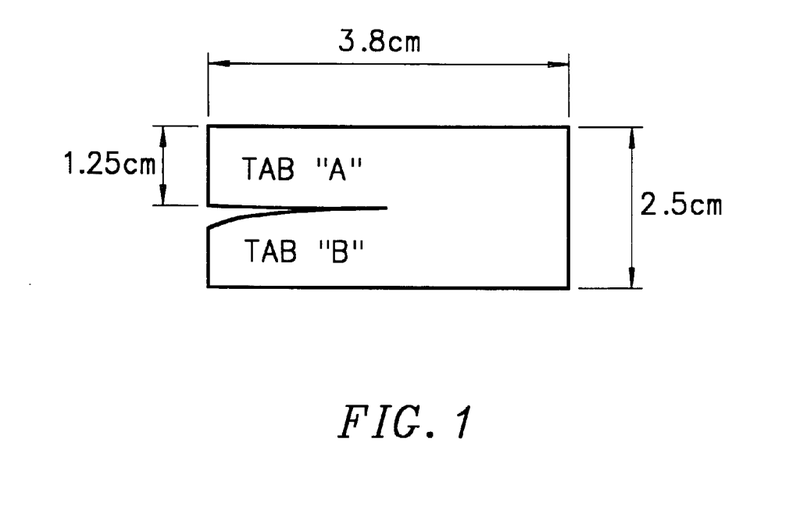
FIG. 1 illustrates the dimensions of test films used to measure the force in the Experimental section below.

The forces required to propagate a tear in the collagen/gelatin films were calculated using a 3.8×2.5 cm rectangular piece from the test film having the shape and dimensions shown in FIG. 1. The force to tear between tabs A and B was measured using a Chatillon tester (TDC 200 test stand fitted with 250 g or 2.25N load cell, DGGS 250 g digital force gauge).

6. and 7. TENSILE STRENGTH AND STRAIN AT FAILURE

Tests were performed with a Chatillon TCD 200 fitted with a digital force gauge (Chatillon Instruments, Greensboro, N.C.), connected to an XY plotter. Film samples were typically 1×3 cm and were glued to polystyrene tabs with cyanoacrylate (Superglue). Films and tabs were hydrated for precisely 1 min. in 0.9% (w/w) saline and blotted briefly. The plastic tabs were clamped in the jaws of the tester, which assured that tensile failure occurred within the sample and not at the point of clamping. Stress was computed as force in Newtons divided by the original cross-sectional area (determined from thickness and width of test films); percent strain at failure was $\Delta l/l_o \times 100$ where $\Delta l$ is the change in length and $l_o$ is the original sample length.

8. LOSS ON DRYING

Weight loss on drying of collagen/gelatin films, raw material collagen, slurries, and solutions were determined by placing the test samples into an oven which had been set at 120° C.±5° C. The sample remained in the oven for at least 20 minutes after the oven had reached its set temperature. Percent loss on drying was calculated using the following formula $$\text{Percent loss on drying} = \frac{(\text{wet sample weight} - \text{dry sample})}{\text{wet sample weight}} \times 100$$

Percent solids was calculated using the following formula $$\text{percent solids} = \frac{\text{dry sample weight} \times 100}{\text{wet sample weight}}$$

9. COLLAGENASE DIGESTION

Film samples were cut into disks 6 mm in diameter, using a steel punch. Such disks typically weighed 2–3 mg and were between 0.04 and 0.07 thick. The sample disks were placed in 2.0 ml of a digestion buffer (Tris-HCl, pH 7.5, 0.05M, containing 0.005M $CaCl_2$) plus 120 ul of a Clostridial collagenase solution. The collagenase was prepared at 300 units/ml in 0.05M Tris-HCl, pH 7.5, containing 0.0005M $CaCl_2$. Enzyme units were as given by the manufacturer, based on hydrolysis of furylacryloyl-Leu-Gly-Pro-Ala. The level of enzyme was sufficient to be in excess for all film samples taken. The sample in buffer and enzyme was incubated with shaking at 37° C. until the sample disk disintegrated, which was scored as digestion time.

The results of these tests are summarized in Table 3 below.

10. PEEL STRENGTH

Measurements were performed on films (2×3 cm) to which polystyrene tabs had been bonded using cyanoacrylate glue (prior to bonding with the argon beam). The polystyrene was approximately 0.5 mm thick, and a hole approximately 4 mm in diameter was punched in the free edge. To measure bonding of the film, the tab was hooked (through the hole) to a digital force gauge (Omega model DFG51-2, 2 lb load cell, Omega Engineering, Inc., Stamford, Conn.). With the patch under no tension, the gauge was set to zero force, and then the gauge was raised manually at a rate of approximately 1 cm/sec to effect a peeling detachment of the film. The gauge was lifted until the film was separated from the tissue. The maximum force registered during the peeling operation was recorded as Newtons of force per cm width of film. Films were welded to warm excised tissue, such as porcine lung or bovine heart muscle using an argon beam coagulator ABC 6400 (CONMED, Ithaca, N.Y.). Peel strength measurements were typically commenced 3 minutes after welding to tissue.

The results of these tests are summarized in Table 2 below.

TABLE 2

| | TEST METHOD | A | B | C | D |
|---|---|---|---|---|---|
| 1. | Thickness(mm) | 0.046 | 0.049 | 0.062 | 0.055 |
| 2. | Swelling (V/V$_0$) | 4.2 | 6.1 | 6.4 | 4.2 |
| 3. | DSC Peak(° C.) | 35.5 | 35.2 | 35.4 | 35.1 |
| 4. | Pliability(mN) | 1.5 | 3.2 | 2.8 | N/A |
| 5. | Tear test(N) | 0.018 | 0.019 | 0.08 | 0.10 |
| 6. | Tensile strength at failure (N/cm$^2$) | 174 | 361 | 242 | 309.1 |
| 7. | Strain at failure(%) | 44 | 97 | 121 | 115 |
| 8. | Loss on drying(%) | 11.9 | 15.5 | 13.6 | 12.7 |
| 9. | Collagenase digestion(min) | 42 | 18 | 22 | N/A |
| 10. | Peel strength(N/cm) | N/A | N/A | 0.12 | N/A |

EXAMPLE 3

Repeat Tests With Different Formulations

Three additional formulations were produced according to the methods set forth in Example 1. These formulations were tested according to the methods set forth in Example 2 and had similar results. The formulations had various starting ratios of collagen and PEG and are summarized in Table 3 below.

TABLE 3

| COLLAGEN (%) | PEG 400 MW (%) |
|---|---|
| 91 | 9 |
| 80 | 20 |
| 67 | 33 |

EXAMPLE 4

Tissue Welding

Tissue welding with argon beam coagulator and peel strength measurements on porcine lung in vitro were performed as follows. Film samples were placed on the tissue of interest, typically porcine lung (see below) or beef heart slices (purchased from a local market.) The tissue of interest was placed in contact with the return electrode of the argon beam coagulator, usually on the underside. Immediately upon placing on the tissue, the film began to hydrate. Welding was preferably performed within 20 sec after placing on tissue, since bonding was a function of film hydration. The spark discharge from the tip of the coagulator was then directed onto a patch at a distance of a few mm between tip and film. The coagulator was typically set at 40 W of power and 2–4 liters/min. of argon gas flow. Other settings were explored, but the strength of the bond achieved was less. The spark discharge was maintained for 2–5 sec per cm$^2$ of film. Application of the argon spark was terminated when the film became desiccated or showed signs of carbonization.

The porcine lung model for in vitro welding tests was as follows. Porcine lung was received on ice from a slaughterhouse, usually within a day of slaughter. The lung was divided at the main bronchus, and one side was used for each test series. A tube was fitted to the largest bronchus, and air was pumped into the lung using a pump (Air Cadet Model 7059-42, Cole-Parmer Instruments, Niles, Ill.) to achieve inflation. The lung was housed in a chamber of clear acrylic, which was mounted on a heated platform. The air pressure lines were also passed through a heated circulating bath. Heated 0.9% aq. sodium chloride was sprayed on the lung tissue at intervals. Tissue temperatures were maintained between 29° C. and 40° C., preferably between 37° C. and 40° C.

To demonstrate that bonding can be achieved by the application of additional energy sources, films were bonded with a heated brass platen. The test device utilized was constructed as follows. Brass blocks with an exposed contact area of 1 cm$^2$ were placed in contact. The lower block was connected to a digital heating controller, which permitted temperature control within 1° C. The upper block was connected to a lever arm to which weights could be attached to vary the compressive force between the blocks. Heating was first applied with the upper and lower blocks in contact. The upper block was heated by conduction from the lower. Two film samples (1 cm×2 cm) were glued to plastic tabs, as described above for tensile testing. The films were then hydrated in 0.9% aq. sodium chloride to achieve a hydration ratio (V/V$_o$) of approximately two, placed in contact with their edges aligned, wrapped in one layer of aluminum foil (0.02 mm thick), and placed between the blocks, which had been equilibrated to a pre-set temperature between 80° C. and 120° C. The foil wrapper prevented the films from sticking to brass blocks. Heating of the apposed, hydrated films was conducted for 10 to 30 seconds. Approximately 100 g of compressive force (1N) was applied during the weld. At the completion of the weld, the apposed film samples were removed from the foil wrapper, mounted in the tensile test apparatus, and the force to peel apart was measured within 5 to 20 min. At the time of the peel test, the sample was at room temperature and the hydration level (V/V$_o$) was still approximately two.

Results of Examples 1, 2, 3, and 4

Table 2 summarizes the properties of granular films prepared by the process of the present invention. Non-granular films were similar. The melting temperatures in DSC confirmed that the collagen had been converted to gelatin during the extended heating step (see below). Resistance to collagenase and the high swelling percentages were consistent with cross-linked gelatin resulting from UV treatment. Films were quite thin to enhance pliability, which was critical for good apposition to irregular tissue sites. Granular films were somewhat opaque in appearance, had a roughened texture on the upper surface, and contained fibrous inclusions up to 1 mm in diameter when viewed in a light microscope. Non-granular films were transparent, were smooth both on upper and lower surfaces, and possessed no inclusions greater than a few microns in diameter.

Figure 3:
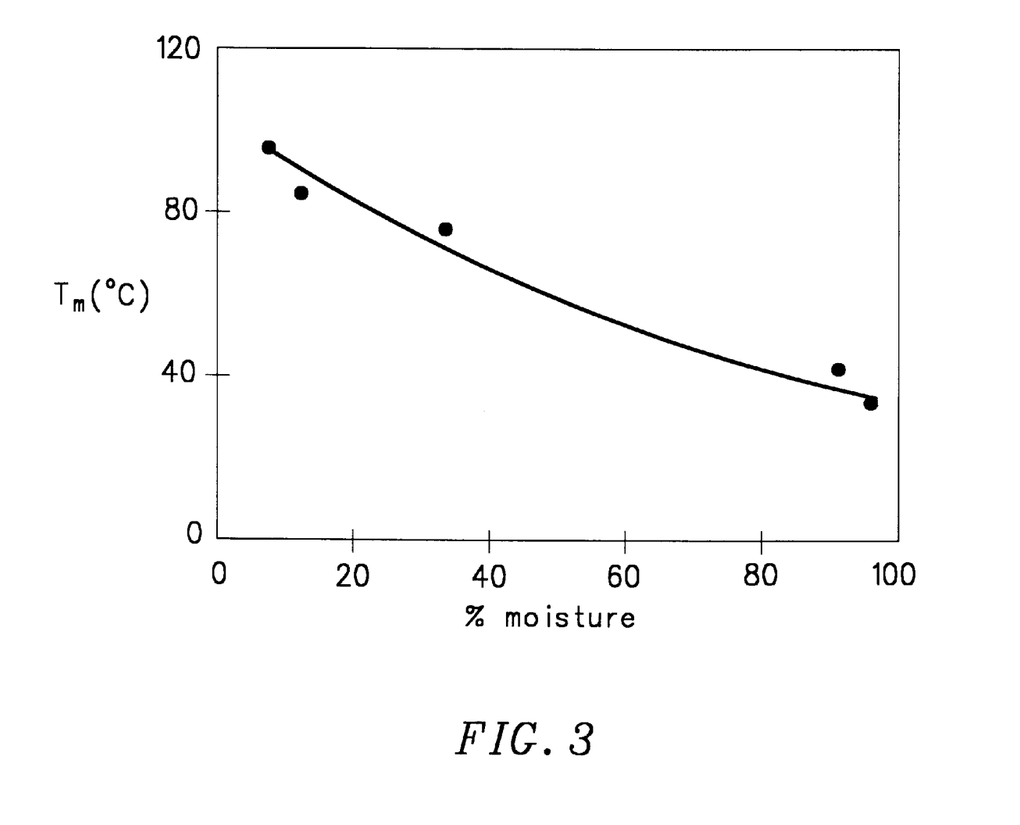
FIG. 3 shows the melting temperature as a function of moisture content for non-granular film.
Figure 4A:
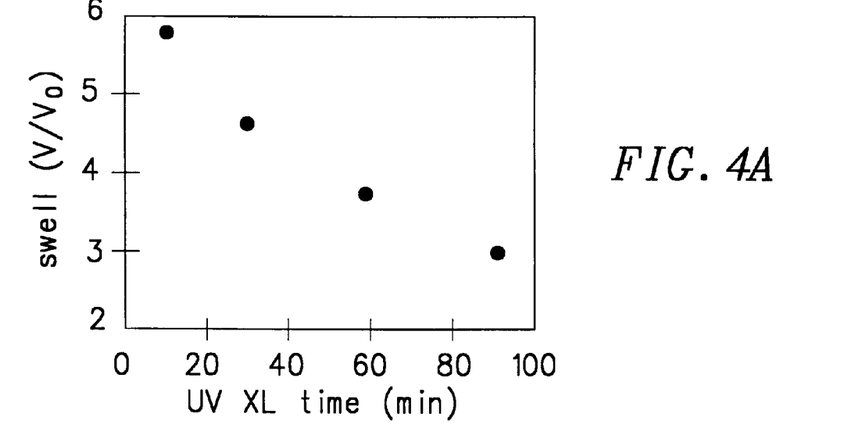
FIG. 4A: Swelling ($V/V_o$) as a function of cross-linking time in UV.
Figure 4B:
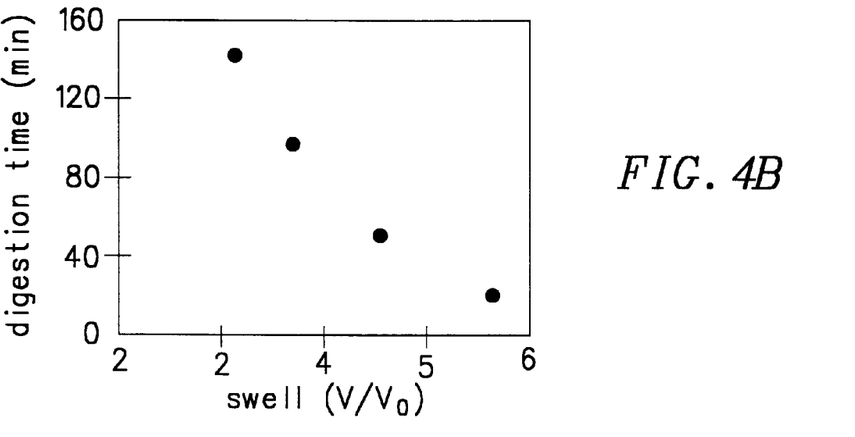
FIG. 4B: Collagenase digestion time vs. swelling ($V/V_o$).
Figure 4C:
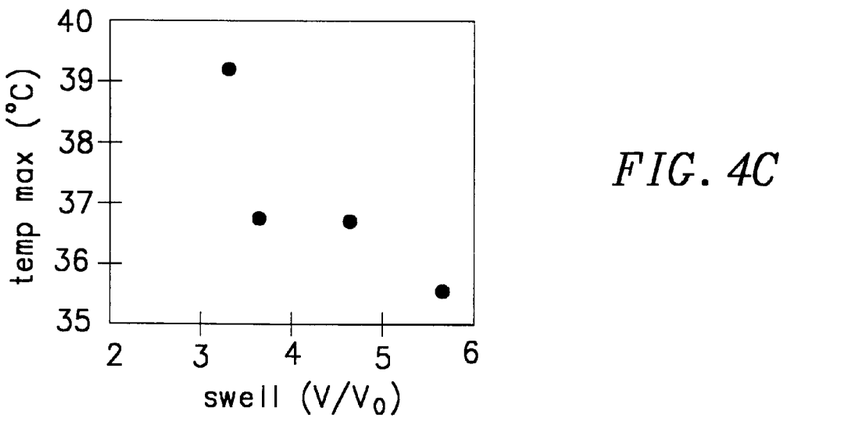
FIG. 4C: Peak melting temperature in DSC vs. ($V/V_o$). Approximate errors in swelling ratio, collagenase digestion time, and DSC melting temperature were 3%, 18%, and 3%, respectively.

The DSC of the cross-linked gelatin of the present invention was compared with that of known collagen and gelatin samples. Kensey-Nash fibrous collagen hydrated with 0.9% sodium chloride to 9–10% solids showed a single major endotherm with a peak melting temperature of 55.7° C.±1.2° C. (n=3; mean and standard deviation) and enthalpy of denaturation 51.8±3.3 J/g. Dynagel gelatin hydrated and tested as above exhibited a broad endotherm with peak temperature 35.3° C.±1.1° C.(n=3) and enthalpy of denaturation of 38.5±4.4 J/g. Because films may be hydrated to different extents on tissue as a function of time of tissue contact, we also examined the effect of hydration level on peak melting temperature (FIG. 3). Film characteristics were greatly affected by the extent of cross-linking (FIG. 4). In general, films swelled less, resisted collagenase more, and melted at higher temperatures as the degree of cross-linking increased.

Figure 2A:
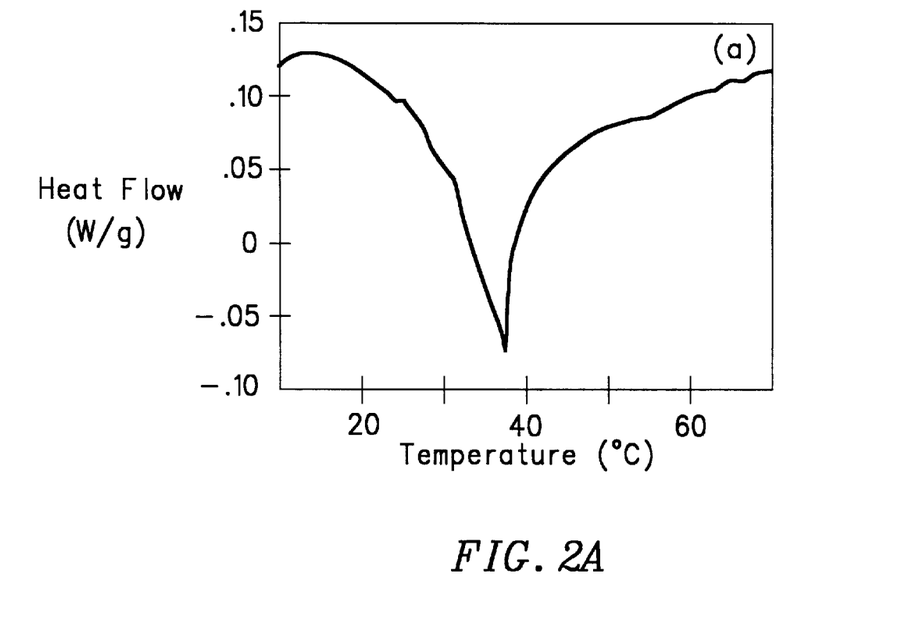
FIGS. 2A–2D depict the DSC of various tissues and granular film. Heating rate: 5° C./min. for FIG. A and 10° C./min. for FIGS. 2B, C, and D.
Figure 2B:
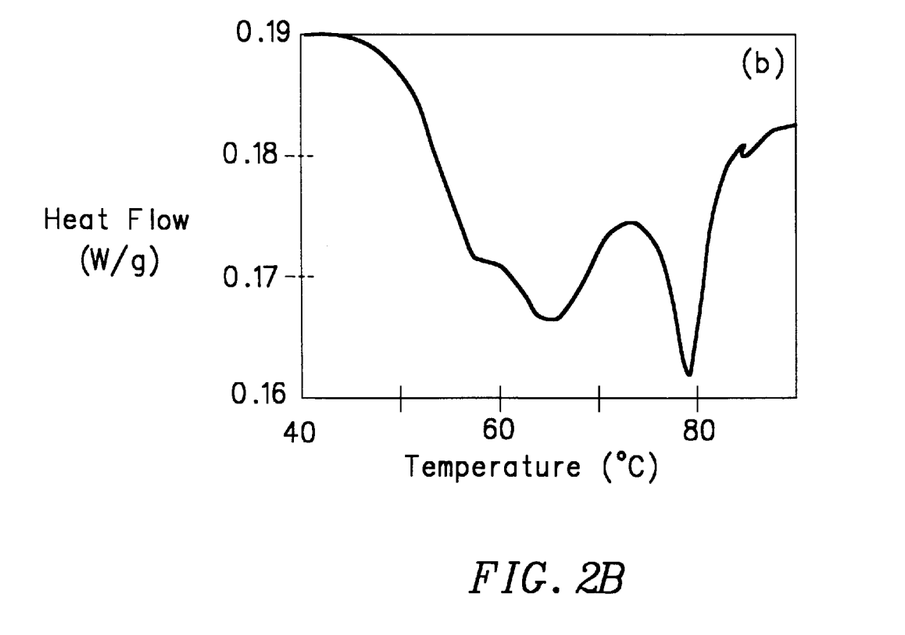
Figure 2C:
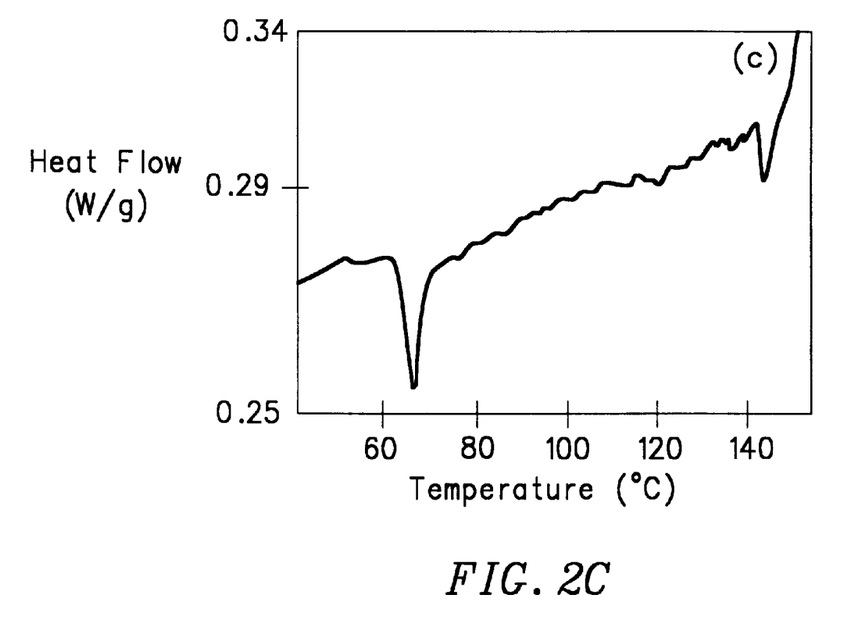
Figure 2D:
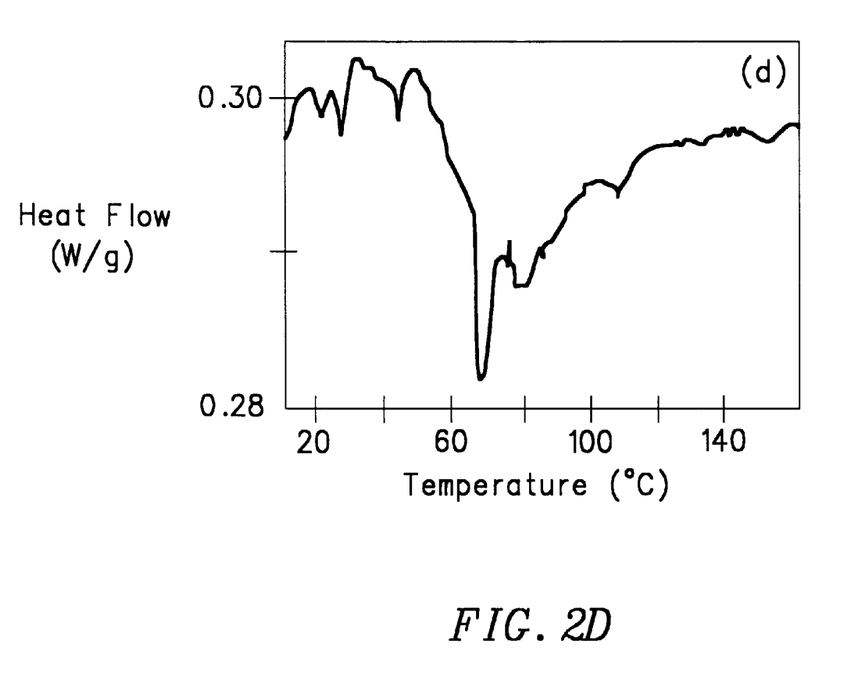
Figure 5A:
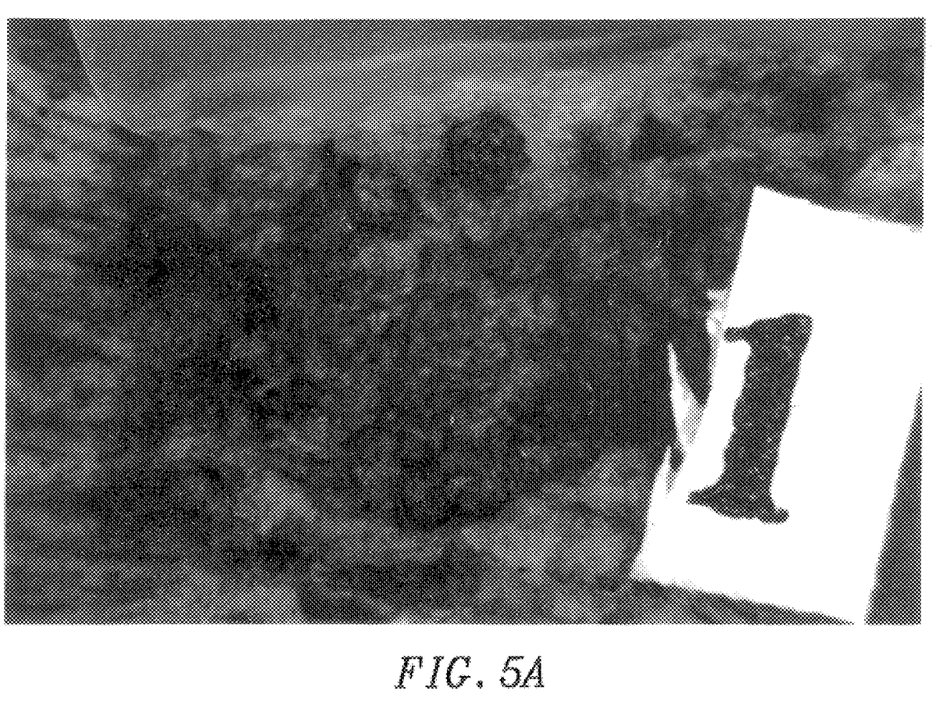
FIG. 5A: Granular film after attachment to beef heart tissue by the argon beam coagulator. An untreated region of the film is visible in the lower part of the figure. Holes created in the film by the argon beam are darker, lighter areas of film are evident between holes.
Figure 5B:
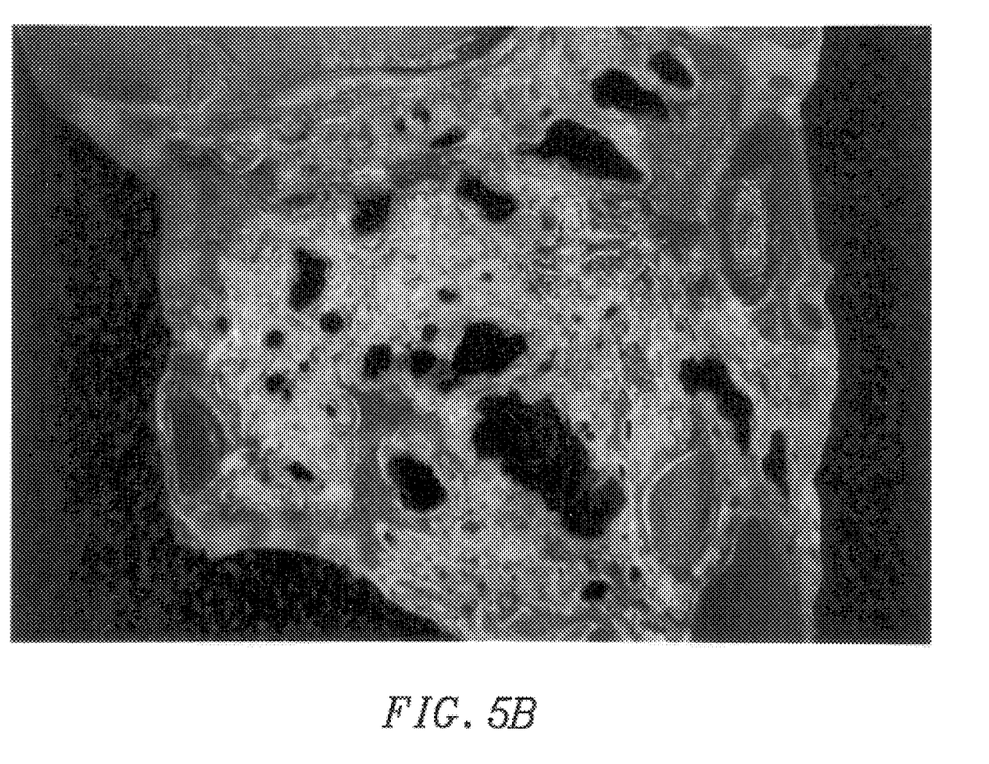
FIG. 5B: Film as in FIG. 5A removed from the beef heart. Holes in film clearly visible.
Figure 5C:
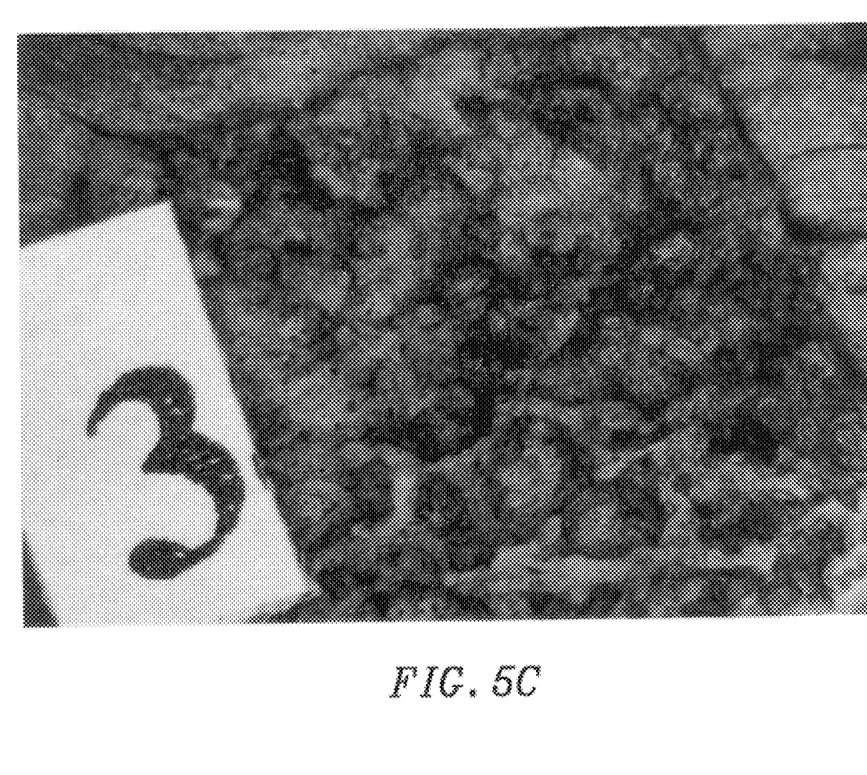
FIG. 5C: Beef heart muscle underlying argon-beam treated film. Lighter areas are coagulum. Darker regions appear to be unaffected by the beam; i.e. these areas have the same appearance as untreated beef heart. Images from Bausch and Lomb Stereo Zoom 7 dissecting microscope at 30×.

During welding on porcine lung or on beef heart, the film changed in appearance, becoming more opaque and melting and shrinking to a limited extent in response to the thermal energy. Tissue underneath the patch was also "melted" or denatured. The material of the patch and the tissue appeared to have intermingled or flowed together during the application of the argon beam. Immediately upon cessation of argon treatment, the temperature of the weld site declined rapidly and returned to that of the surrounding tissue within seconds, resulting in a coagulum, or congealed mixture, of the two components. The fusion of tissue and film elements was easily observed when the bonded film was peeled away from the tissue, the film-tissue interface being visualized in a dissecting microscope at 10–20×. In some regions of the film, congealed tissue protein appeared to have penetrated into holes in the film and solidified there, creating a mechanical bond (FIGS. 5A, 5B, and 5C). Tissue appeared to be denatured to a depth of 0.2 to 0.7 mm, depending on the duration of energy application and the power setting. DSC of lung and heart tissue showed that these tissues have components which denature over a wide range of temperatures from 50° C. to 150° C. (See, FIGS. 2B, 2C, and 2D.) Although it is difficult to determine the temperature of tissue subjected to the argon beam, vaporization of water is evident, and for long exposures, points of carbonization appear, which suggests temperatures above 100° C. in localized domains. The range of peel bond strengths for Formulation C obtained after 3 min. on irrigated tissue was 0.12±0.05 N/cm (mean and standard deviation n=6). Tissue was wet but not flushed with 0.9% aq. sodium chloride. A jet or spray of saline solution was applied within about 10 sec after completion of the weld. Occasionally, underlying tissue was torn (failed cohesively) as the film was peeled off. Tests in which welded films were not disturbed for up to one hour (with continued periodic irrigation) showed that the bond was maintained and the film was intact.

The films described above were the result of multiple trials, in which film properties were varied. It was observed that films less than about 0.04 mm thick were easy to weld, but they partially disintegrated during the application of the argon beam, and they failed cohesively in peel bond tests. Films greater than 0.2 mm thick presented a conductive barrier to the argon beam, and the spark could only find a conductive path at the edge of the film. As a result, such films were only bonded to tissue at the edges, and once the edge bond was broken, they were readily detached from the tissue. Apposition to tissue appeared to be essential for achieving a good bond. The effect of UV cross-linking was also examined. Films which were not cross-linked bonded very well and with a shorter duration of argon beam application. Such films, however, had poor cohesive strength during peel tests. Films which were cross-linked longer than about 40 minutes resulting in about 4000 mJ/cm² or greater as used herein had good cohesive strength but exhibited weaker bond strengths or no bonding. The degree of film hydration on the tissue was also an important variable. Kinetic swelling experiments on hydrated tissue and in physiological saline showed that films hydrated to $V/V_o=1.5$ to 2 (corresponding to 30 and 50% moisture) within 10–30 sec on tissue, depending on the frequency of irrigation. At hydration levels near this value, e.g. from $V/V_o=1.5$ to 2.5, good bonding was achieved. At higher hydration levels, e.g. $V/V_o=4–6$, which occurred after 2–4 min. on the tissue, bonding was much poorer. The ideal duration of application of the argon beam was about 2–5 sec/cm² for granular films with the properties given in Table 2. For non-granular films between 0.04 and 0.06 mm thick, 1–3 sec/cm² gave better bonds. For films which were thicker or more granular (less homogenization) or more highly cross-linked, the optimal weld duration was 5–7 sec/cm². Power settings higher than 40 W tended to cause disintegration of films and deeper denaturation of tissue. Lower power settings were not possible with the Birtcher coagulator. With other argon beam instruments which permitted lower power, it was found that melting and intermingling of film and tissue were inadequate to produce a satisfactory bond. Granularity of films also affected the optimum welding time. Granular films required longer energy application times compared to non-granular films. Non-granular films had poor cohesive strength during peel test experiments, compared to granular films.

It should be noted that spurious results can be obtained in vitro if the tissue is too cold or too dry. Peel strengths up to 1.0 N/cm may be observed. However, if the tissue is maintained near physiological temperature and hydration (simulating in vivo application) such high peel bond strengths are not observed.

Initial studies using hot brass platen devices were performed to determine approximate conditions for bonding of apposed non-granular films. Films were hydrated to $V/V_o=$ 1.5 to 2.5 (to simulate ideal film hydration during argon beam welding) and heated for 20 sec over a range of temperatures. Films were judged to be bonded if they remained adherent after at least 20 min. of agitation in 0.9% sodium chloride at 37° C. Welding temperatures were varied from 70° C. to 120° C. in 10° C. increments. Stable bonds were formed between 100° C. and 120° C. Above 110° C., films began to disintegrate during heating. An examination of the effect of degree of hydration on bonding showed that a minimum moisture content was required; i.e. $V/V_o$ values of 1.3 or greater were necessary to effect a bond. ("Dry" films were in equilibrium with atmospheric humidity and contained 9–14%; $V/V_o=1.1$). Above $V/V_o=2$, the bond stability (film-to-film adherence in 37° C. saline) appeared to decrease.

Figure 6A:
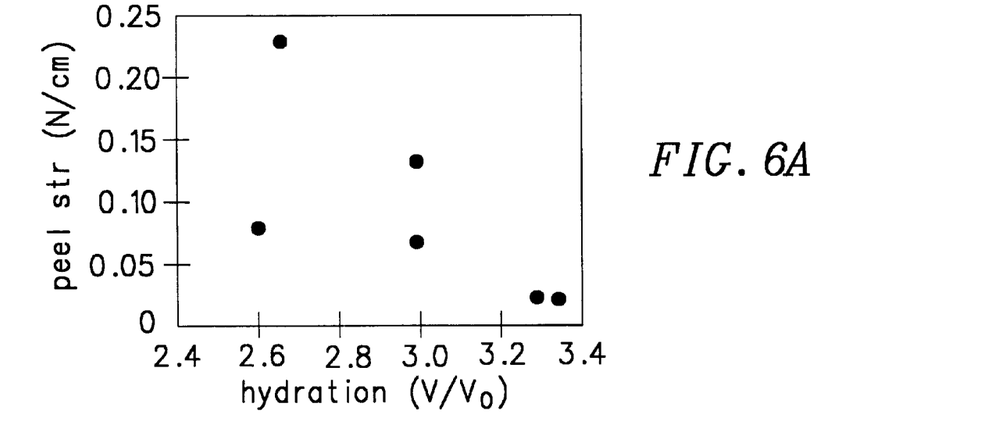
FIG. 6A: Peel bond strength vs. hydration, smooth side to smooth side apposition, 100° C., 20 sec.
Figure 6B:
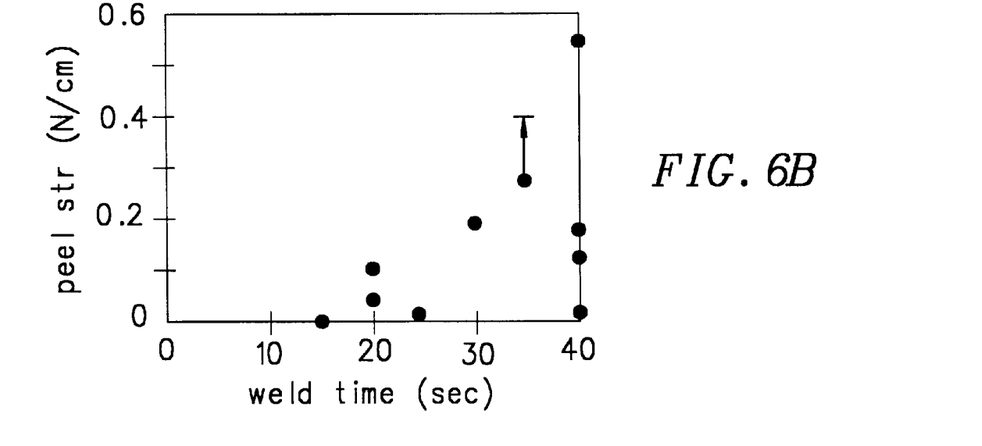
FIG. 6B: Peel bond strength vs. weld time, smooth side to smooth side, 110° C., $V/V_o=3\pm0.5$.
Figure 6C:
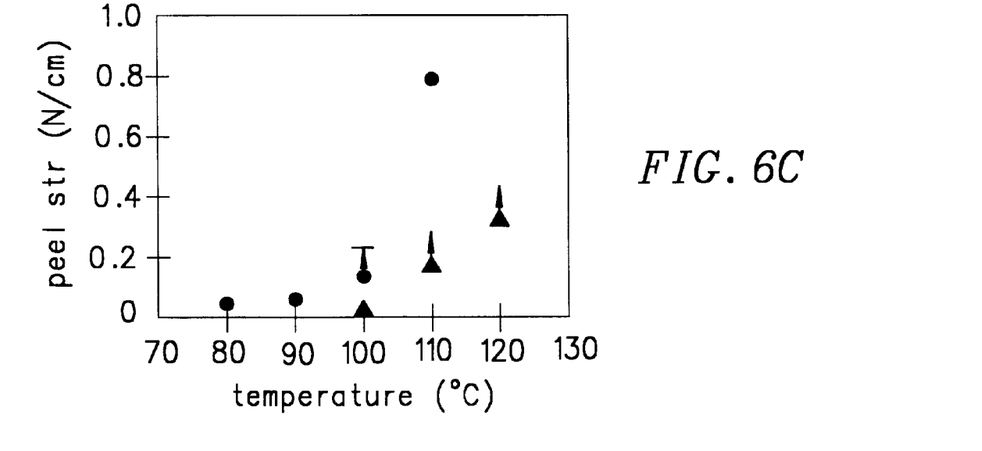
FIG. 6C: Peel bond strength vs. weld temperature, $V/V_o=3\pm0.3$, 30 .sec, smooth side to smooth side, 0; rough side to rough side, Δ. Errors in measurements can be inferred from the scatter; they were of the order of 0.1 to 0.2 N/cm.

Peel strengths of the bonds were also tested. This was only partly successful, since the film cohesive strength was not much greater than the peel bond strengths created. Nevertheless, the same general trends were observed; namely, hydration levels between $V/V_o=1.5$ and 2.5, temperatures between 90° C. and 110° C., and weld durations between 20 and 30 sec (for a 1 cm² area) gave the best results (FIGS. 6A–6C). Low temperatures, short weld times, and hydration levels below $V/V_o=1.5$ and above $V/V_o=2.5$ gave weak bonds or no bonds. At high temperatures or long weld times, the films began to disintegrate. Granular films required longer weld times and higher temperatures to achieve stable and strong bonds, compared to non-granular films.

Other biomaterials in sheet or sponge form were tested as follows. All tests described below were on porcine lung. Various sheet-form materials were tested; commercially available gelatin sponges (Superstat®) or collagen fibrous mats (Avitene®) did not form bonds to tissue. Calfskin, cross-linked or not, curled extensively under application of the argon beam and apposition to tissue was lost, preventing bond formation. Sheets of oxidized cellulose (Surgical®), intended for prevention of surgical adhesions, disintegrated upon application of the argon beam. Sheet stock of implantable grade polypropylene, polyethylene, silicone, and Gortex® Soft Tissue Patch were unsuitable. Holes were created in the sheets if they were thin enough, but no bonding resulted. Meshes and fluted tubes of the above materials and of Dacron®, intended for vascular grafts or hernia repair, were also unsatisfactory.

Although the foregoing invention has been described in detail for purposes of clarity of understanding, it will be obvious that certain modifications may be practiced within the scope of the appended claims.

What is claimed is:

1. A gelatin film characterized by:

a film thickness in the range from 0.03 mm to 0.2 mm;

a pliability in the range from 1 mN to 4 mN; and at least one characteristic selected from the group consisting of:

a moisture content in the range from 11% to 16%;

an elasticity in the range from 30% to 150%;

a tensile strength in the range from 150 N/cm$^2$ to 260 N/cm$^2$;

a melting temperature in the range from 33° C. to 40° C.;

a collagenase digestion time in the range from 10 min. to 40 min, and a degree of swelling (V/V$_o$) in the range from 4.5 to 6.5.

2. A gelatin film as in claim 1, wherein the gelatin is cross-linked.

3. A gelatin film as in claim 1, wherein the gelatin is granular.

4. A gelatin film as in claim 1, wherein the gelatin is non-granular.

5. A gelatin film as in claim 1, wherein the gelatin film comprises a plasticizer.

6. A gelatin film as in claim 5, wherein the gelatin comprises granular cross-linked gelatin having a plasticizer content in the range from 5% by weight to 40% by weight and a thickness in the range from 0.03 mm to 0.2 mm.

7. A gelatin film as in claim 6, consisting essentially of gelatin which has been produced from collagen and the plasticizer, where residual collagen may be present in the gelatin sheet.

8. A gelatin film as in claim 6, wherein the plasticizer is selected from the group consisting of polyethylene glycol, sorbitol, and glycerine.

9. A gelatin film as in claim 8, wherein the plasticizer is polyethylene glycol 400 at from 5% by weight to 40% by weight.

10. A package comprising:

a sterile sheet of gelatin film according to any one of claims 1 to 9; and a container enclosing the gelatin sheet, wherein the sterility and moisture content of the gelatin film are preserved within the container.

11. A method for sealing tissue, said method comprising positioning a film according to any of claims 1 to 9 to a target region in tissue; and applying energy to the film over a region and in an amount sufficient to immobilize the film on the tissue.

12. A method as in claim 11, wherein the target region is a surgical site.

13. A method as in claim 12, wherein the target region is in tissue selected from the group consisting of muscle, skin, epithelial tissue, connective or supporting tissue, nerve tissue, ophthalmic and other sense organ tissue, vascular and cardiac tissues, gastrointestinal organs and tissue, pleura and other pulmonary tissue, kidney, endocrine glands, male and female reproductive organs, adipose tissue, liver, pancreas, lymph, cartilage, bone, oral tissue, and mucosal tissue.

14. A method as in claim 12, wherein the surgical site is open to permit both positioning of the film and applying energy to the film.

15. A method as in claim 2, further comprising forming at least two percutaneous penetrations to the target region, introducing a viewing scope through one of said penetrations, viewing the target region using said viewing scope, positioning the film through another of the penetrations while viewing, and applying energy through another of said penetrations while viewing.

16. A method as in claim 11, further comprising a step of shaping the film to conform to the dimensions of the target region prior to positioning the film over said target region.

* * * * *